US00PP33520P3

(12) United States Plant Patent
Post

(10) Patent No.: US PP33,520 P3
(45) Date of Patent: Sep. 28, 2021

(54) ***CHRYSANTHEMUM* PLANT NAMED 'DLFJAMD3'**

(50) Latin Name: ***Chrysanthemum* X *morifolium***
Varietal Denomination: DLFJAMD3

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 17/089,694

(22) Filed: Nov. 4, 2020

(65) Prior Publication Data

US 2021/0136982 P1 May 6, 2021

Related U.S. Application Data

(60) Provisional application No. 62/973,983, filed on Nov. 5, 2019.

(51) Int. Cl.
*A01H 5/02* (2018.01)
*A01H 6/14* (2018.01)

(52) U.S. Cl.
USPC ..... Plt./297

(58) Field of Classification Search
USPC ..... Plt./297
See application file for complete search history.

*Primary Examiner* — Susan McCormick Ewoldt
(74) *Attorney, Agent, or Firm* — C. Anne Whealy

(57) ABSTRACT

A new and distinct cultivar of *Chrysanthemum* plant named 'DLFJAMD3', characterized by its upright plant habit; vigorous growth habit and rapid growth rate; dark green-colored leaves; uniform and freely flowering habit; strong upright flowering stems with numerous inflorescences; pom-pon-type inflorescences with light purple-colored ray florets that when developing are distally darker purple in color giving a bi-colored appearance; relative tolerance to low and high production temperatures; resistance to *Fusarium* Wilt and White Rust; and good postproduction longevity.

2 Drawing Sheets

Figure 1:
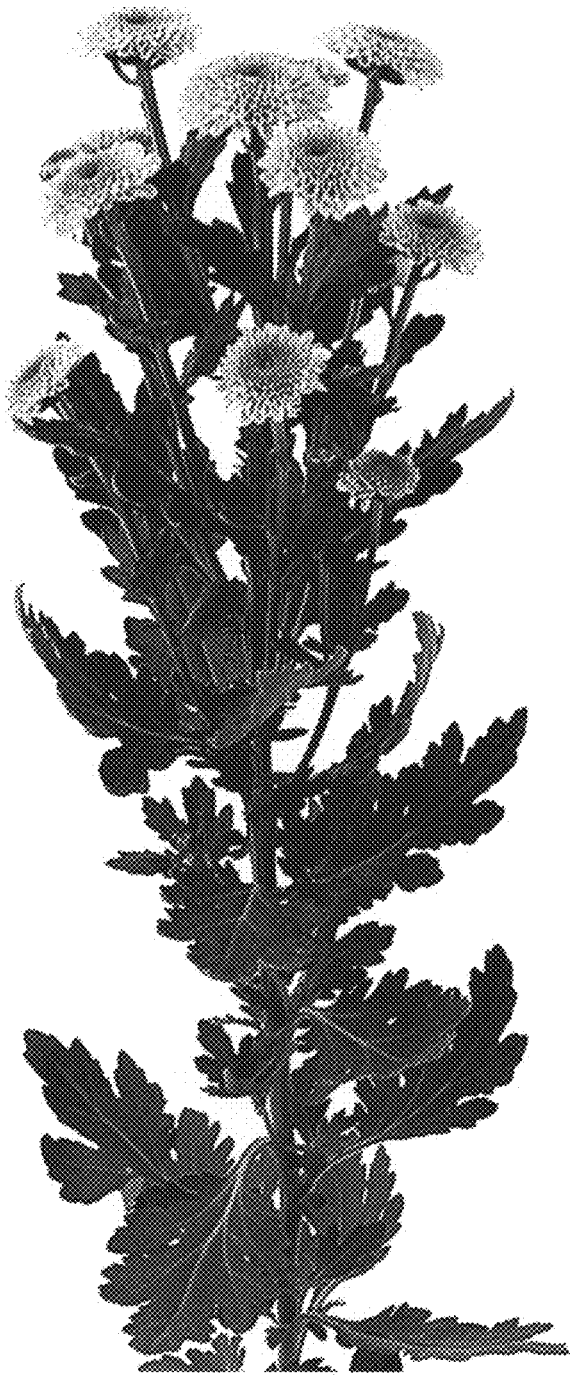
Figure 2:
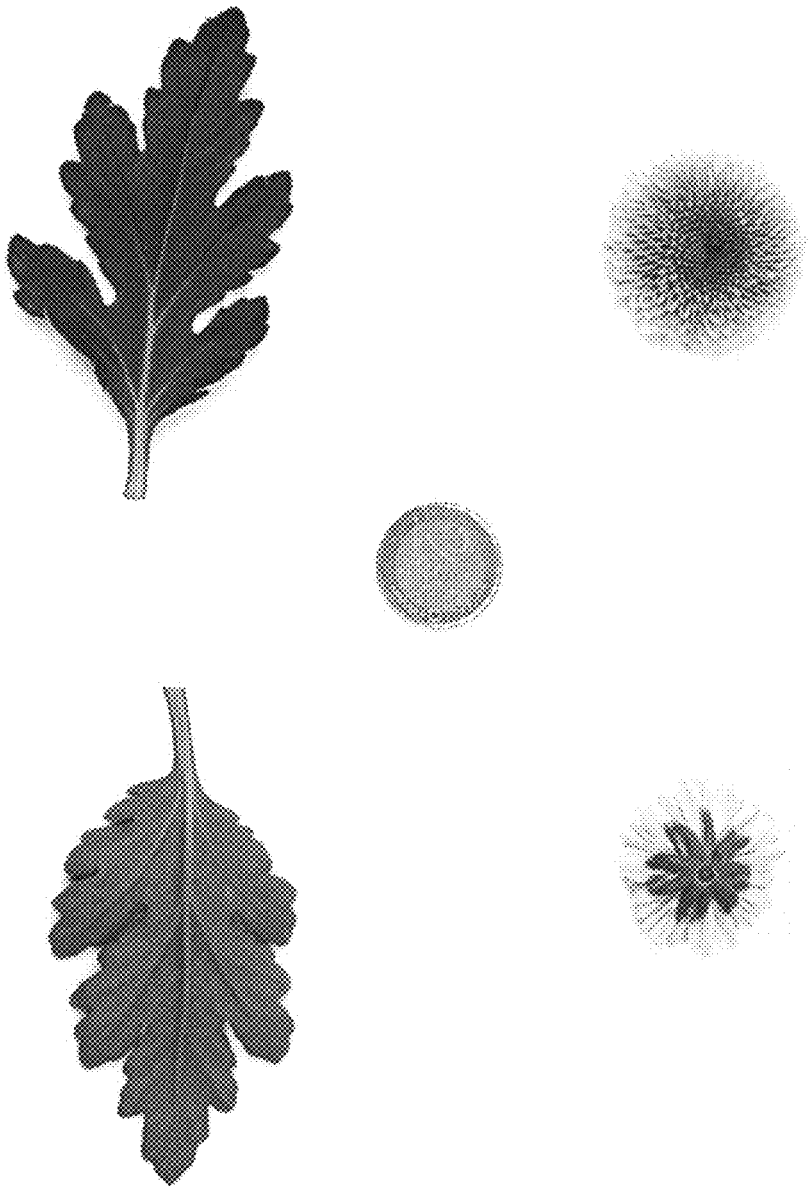

Botanical designation: *Chrysanthemum* X *morifolium*.
Cultivar denomination: 'DLFJAMD3'.

CROSS-REFERENCED TO CLOSELY-RELATED APPLICATIONS

Title: Varieties of *Chrysanthemum* Plants
Inventor/Applicant: Arie Gerard Post
Filed: Nov. 5, 2019
Ser. No. 62/973,983
Inventor/Applicant hereby claim the benefit of this provisional U.S. Patent Application.

STATEMENT REGARDING PRIOR DISCLOSURES BY INVENTOR/APPLICANT & ASSIGNEE

An European Community Plant Breeder's Rights application for the instant plant was filed by the Assignee, Deliflor Royalties B. V. of Maasdijk, The Netherlands on Jul. 29, 2019, application number 2019/1843. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFJAMD3'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant is a naturally-occurring whole plant mutation of *Chrysanthemum* x *morifolium* 'DLFJAM3', disclosed in U.S. Plant Pat. No. 31,943. The new *Chrysanthemum* plant was discovered and selected as a single flowering plant from within a population of plants of 'DLFJAM3' in a controlled greenhouse environment in Maasdijk, The Netherlands in March, 2018.

Asexual reproduction of the new *Chrysanthemum* plant by vegetative terminal cuttings since March, 2018 has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFJAMD3'. These characteristics in combination distinguish 'DLFJAMD3' as a new and distinct *Chrysanthemum* plant:

1. Upright plant habit.
2. Vigorous growth habit and rapid growth rate.
3. Dark green-colored leaves.
4. Uniform and freely flowering habit.
5. Strong upright flowering stems with numerous inflorescences.
6. Pompon-type inflorescences with light purple-colored ray florets that when developing are distally darker purple in color giving a bi-colored appearance.
7. Relatively tolerant to low and high production temperatures.
8. Resistant to *Fusarium* Wilt and White Rust.
9. Good postproduction longevity.

Plants of the new *Chrysanthemum* differ from plants of the mutation parent, 'DLFJAM3', in ray floret color as plants of the new *Chrysanthemum* have light purple-colored ray florets that when developing are distally darker purple in color whereas ray florets of 'DLFJAM3' are lighter and paler purple in color.

Plants of the new *Chrysanthemum* can be compared to plants of *Chrysanthemum* X *morifolium* 'DLFIZABA', not patented. In side-by-side comparisons, plants of the new *Chrysanthemum* differ primarily from plants of 'DLFIZABA' in ray floret color as plants of the new *Chrysanthemum* have light purple-colored ray florets that when developing are distally darker purple in color whereas ray florets of 'DLFIZABA' are lighter and paler purple in color. In addition, plants of the new *Chrysanthemum* have smaller inflorescences than plants of 'DLFIZABA'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet comprises a side perspective view of a typical flowering stem of 'DLFJAMD3' grown as a spray-type cut flower.

The photograph on the second sheet is a close-up view of upper (top of the photographic sheet) and lower (bottom of the photographic sheet) surfaces of typical leaves (left) and inflorescences (right).

DETAILED BOTANICAL DESCRIPTION

The aforementioned photographs and following observations and measurements describe plants grown during the late spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were seven weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFJAMD3'.

Parentage: Naturally-occurring whole plant mutation of *Chrysanthemum* x *morifolium* 'DLFJAM3', disclosed in U.S. Plant Pat. No. 31,943.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 22° C.

*Time to produce a rooted young plant, winter*.—About 15 days at temperatures about 20° C.

*Root description*.—Fine, fibrous; typically light brown in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative pompon-type cut flower that is typically grown as a single stem spray-type; upright plant habit; vigorous growth habit and rapid growth rate.

*Plant height, soil level to top of foliar plane*.—About 75.3 cm.

*Plant height, soil level to top of inflorescence plane*.—About 79.2 cm.

*Plant (spray) diameter*.—About 16.3 cm.

*Flowering stem length*.—About 74 cm.

*Flowering stem diameter*.—About 6 mm.

*Flowering stem internode length*.—About 2.1 cm.

*Flowering stem strength*.—Strong.

*Flowering stem aspect*.—Erect.

*Flowering stem texture and luster*.—Moderately to densely pubescent; moderately glossy.

*Flowering stem color, developing*.—Close to 144A.

*Flowering stem color, developed*.—Close to between 143A and 144A slightly tinged with close to 177B.

*Leaf description*.—Arrangement: Alternate; simple. Length: About 7.1 cm. Width: About 4.5 cm. Shape: Oblong to broadly ovate. Apex: Abruptly acute. Base: Attenuate. Margin: Palmately lobed, coarsely serrate to dentate; sinuses convergent to parallel and medium to deep in depth. Texture and luster, upper surface: Moderately pubescent, not rugose; moderately velvety; slightly glossy. Texture and luster, lower surface: Densely pubescent, prominent venation; slightly velvety; very slightly glossy. Venation pattern: Pinnate, reticulate. Color: Developing leaves, upper surface: Close NN137A. Developing leaves, lower surface: Close to 147B. Fully developed leaves, upper surface: Slightly darker than NN137A; venation, close to 147C. Fully developed leaves, lower surface: Close to 147B; venation, close to 146C. Petioles: Length: About 1.8 cm. Diameter: About 2 mm by 3 mm. Strength: Moderately strong. Texture and luster, upper and lower surfaces: Densely pubescent; moderately glossy. Color, upper surface: Close to 146B to 146C; edges, close to NN137A. Color, lower surface: Close to 146B to 146C; edges, close to 137A. Stipules: Quantity and appearance: Two leafy stipules, opposite, at the petiole attachment to the stem. Length: About 6 mm.

Width: About 8 mm. Shape: Reniform. Texture and luster, upper surface: Moderately pubescent, not rugose; moderately velvety; slightly glossy. Texture and luster, lower surface: Densely pubescent, prominent venation; slightly velvety; very slightly glossy. Color, upper surface: Slightly darker than NN137A. Color, lower surface: Close to 147B.

Inflorescence description:

*Appearance*.—Decorative pompon-type inflorescence form with narrowly obovate to oblanceolate-shaped ray florets and tubular disc florets; inflorescences borne perpendicular to peduncles and face mostly upright to slightly outwardly; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 38 days later when grown as a spray-type.

*Postproduction longevity*.—Good postproduction longevity; in an interior environment, inflorescences and foliage will maintain good color and substance for about two weeks; inflorescences persistent.

*Quantity of inflorescences*.—Freely flowering habit; when grown as a spray-type, about 15 inflorescences develop per flowering stem.

*Inflorescence size*.—Diameter: About 4.1 cm. Depth (height): About 1.7 cm. Disc diameter: About 2 mm; inconspicuous.

*Receptacles*.—Height: About 5 mm. Diameter: About 7 mm. Shape: Flattened globular. Color: Close to 145B and 145C.

*Inflorescence buds*.—Height: About 9 mm. Diameter: About 1.4 cm. Shape: Flattened globular. Texture and luster: Distally, smooth and glabrous; proximally, moderately pubescent; moderately glossy. Color: Close to 137A to 137D; immature ray florets, close to 151D and 70B.

*Ray florets*.—Quantity and arrangement: About 420 arranged in about eleven whorls. Length: About 1.4 cm; varying between 0.6 cm and 1.9 cm. Width: About 4.5 mm; varying between 1 mm and 8 mm. Shape: Narrowly obovate to oblanceolate; strongly involute and moderately to strongly carinate. Apex: Obtuse to shallowly emarginate. Base: Attenuate. Margin: Entire; not undulate. Aspect: Initially upright to about 40° from vertical. Texture and luster, upper surface: Smooth, glabrous; moderately velvety; matte. Texture and luster, lower surface: Smooth, glabrous; slightly velvety; very slightly glossy. Color: When opening, upper surface: Close to 75B; distally, close to 75A to 75B. When opening, lower surface: Close to 75B. Fully opened, upper surface: Close to 75B to 75C; venation, similar to lamina colors; color becoming closer to 76C with development. Fully opened, lower surface: Close to between 75C and 76B; venation, similar to lamina colors; color does not change with development.

*Disc florets*.—Quantity and arrangement: About five to ten at the center of the receptacle; disc florets inconspicuous. Length: About 4 mm. Diameter: About 1 mm. Shape: Lower 80% fused into a tube; upper 20% free. Apex: Narrowly acute. Margin, free-part: Entire. Texture and luster, inner and outer surfaces: Smooth, glabrous; glossy. Color, when opening, inner and outer surfaces: Distally, close to 144C; at the apex, close to 144A; and proximally, close to 145B. Color, fully opened, inner and outer surfaces: Distally, close to 144B and proximally, close to 145B.

*Involucral bracts*.—Quantity and arrangement: About 32 arranged in about two whorls. Length: About 1.1 cm. Width: About 4.5 mm. Shape: Narrowly ovate. Apex: Obtuse. Base: Cuneate. Margin: Entire. Texture and luster, upper surface: Smooth, glabrous; glossy. Texture and luster, lower surface: Moderately pubescent; matte. Color, upper surface: Close to 146B to 146D; margins, translucent and close to 157D and N199A. Color, lower surface: Close to 137A and NN137B; margins, translucent and close to 157D and N199A.

*Peduncles*.—Length, terminal peduncle: About 5.2 cm. Diameter, terminal peduncle: About 3 mm. Length, third peduncle: About 6.5 cm. Diameter, third peduncle: About 3 mm. Strength: Strong. Aspect, terminal peduncle: Mostly upright. Aspect, third peduncle: About 30° from the flowering stem axis. Texture and luster: Densely pubescent; moderately glossy. Color: Close to 143A.

*Reproductive organs*.—Androecium: Present on disc florets only. Quantity: About five per floret. Filament length: About 1.5 mm. Filament color: Close to 145D. Anther size: About 0.5 mm by 1.5 mm. Anther shape: Narrowly oblong. Anther color: Close to 154D. Pollen amount: None observed. Gynoecium: Present on both ray and disc florets. Quantity: One per floret. Pistil length: About 5 mm. Style length: About 4.5 mm. Style color: Close to 145D. Stigma diameter: About 1 mm. Stigma shape: Cleft, decurrent. Stigma color: Close to 153D. Ovary color: Close to 157A.

*Seeds and fruits*.—To date, seed and fruit production have not been observed on plants of the new *Chrysanthemum*.

Pathogen & pest resistance: Plants of the new *Chrysanthemum* have been observed to be resistant to *Fusarium* Wilt (*Fusarium oxysporum* spp. *chrysanthemi* (FoNL1)) and White Rust (*Puccinia horiana* (PhNL1 and PhBE6)). To date, plants of the new *Chrysanthemum* have not been observed to be resistant or tolerant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFJAMD3' as illustrated and described.

* * * * *